United States Statutory Invention Registration [19]

[11] Reg. Number: H53

Franko-Filipasic et al. [45] Published: Apr. 1, 1986

[54] PROCESSES FOR PRODUCING HERBICIDE INTERMEDIATES

[75] Inventors: Borivoj R. Franko-Filipasic, Morrisville, Pa.; Sol A. Mednick, Willingboro; James Snyder, Yardville, both of N.J.

[73] Assignee: FMC Corporation, Philadelphia, Pa.

[21] Appl. No.: 582,115

[22] Filed: Feb. 21, 1984

[51] Int. Cl.[4] ..... C07D 261/04; C07D 261/10; C07D 261/12; C07D 413/00

[52] U.S. Cl. ..... 548/243; 562/520

[56] References Cited

U.S. PATENT DOCUMENTS

| | | | |
|---|---|---|---|
| 2,449,163 | 9/1948 | Ford | 562/520 |
| 2,876,241 | 3/1959 | Koch et al. | 260/413 |
| 3,444,187 | 5/1969 | Weyanagi et al. | 548/243 |
| 4,405,357 | 9/1983 | Chang | 71/88 |

FOREIGN PATENT DOCUMENTS

| | | | |
|---|---|---|---|
| 7019292 | 7/1970 | Japan | 548/243 |

OTHER PUBLICATIONS

Matsubara, et al., "Synthesis trimethylacetic acid," *Chem. Abst.* 74: 75977K (1971)

Moller, von Karl Erich, "Kochschen Carbonsauresynthese," *Brennstoff-Chemie* 1 (47) (1966).

Plattner, et al., "Synthesen des 4-Amino-3-isoxazolidinons," *Helv. Chim. Acta.* 40, 1531 (1957).

G. A. Olah, *Friedel-Crafts and Related Reactions,* vol. 3, part 2, Interscience, New York, 1964, pp. 1272-1291.

R. O. Clinton and S. C. Laskowski, "The Preparation of Methyl Esters", *J. Am. Chem. Soc., 70,* 3135 (1948).

*Primary Examiner*—John F. Terapane
*Assistant Examiner*—Susan Wolffe
*Attorney, Agent, or Firm*—Robert M. Kennedy; H. Robinson Ertelt; Robert L. Andersen

[57] ABSTRACT

Processes for producing 4,4-dimethyl-3-isoxazolidinone and intermediates for it from known and inexpensive starting materials are described and exemplified.

12 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESSES FOR PRODUCING HERBICIDE INTERMEDIATES

The present invention relates to novel processes for producing 4,4-dimethyl-3-isoxazolidinone and intermediates therefor in good yields. 4,4-Dimethyl-3-isoxazolidinone is a useful intermediate for certain herbicidal 4,4-dimethyl-2-substituted-3-isoxazolidinones including compounds disclosed in U.S. Pat. No. 4,405,357, incorporated herein by reference.

Among the herbicidal compounds disclosed in the U.S. patent above are compounds of the formula

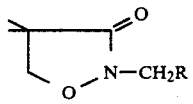

I wherein R is an optionally substituted phenyl radical. In one compound of particular merit R is a 2-chlorophenyl radical. The compounds of formula I were disclosed in the patent as being prepared by one or the other of two general methods:

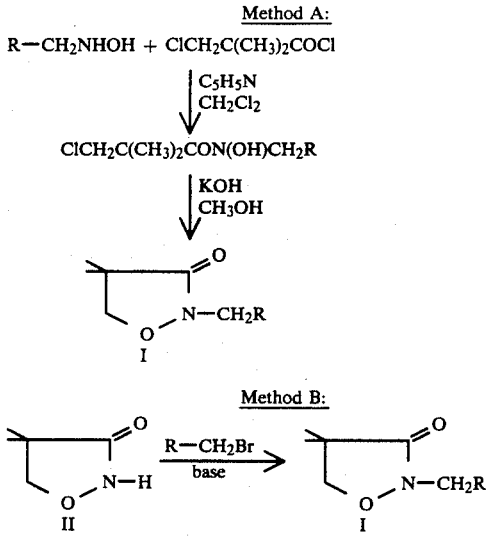

In Method A, an N-(substituted-methyl)hydroxylamine is allowed to react with 3-chloro-2,2-dimethylpropionyl chloride in the presence of pyridine and methylene chloride to give a 3-chloro-N-(substituted-methyl)-N-hydroxy-2,2-dimethylpropanamide which is treated with potassium hydroxide in methanol to afford the compound of formula I. The compound wherein R is 2-chlorophenyl was described as being prepared in this manner.

In Method B, 4,4-dimethyl-3-isoxazolidinone, formula II, is N-alkylated with $RCH_2Br$ in the presence of a base, such as potassium carbonate, to give the compound of formula I. 4,4-dimethyl-3-isoxazolidinone was prepared by Method A except that hydroxylamine was used in place of N-(substituted-methyl)hydroxylamine.

The 3-chloro-2,2-dimethylpropionyl chloride starting material in Methods A and B above was prepared by treatment of the corresponding free acid with thionyl chloride. Preparation of the acid is not disclosed in the patent. However, U.S. Pat. No. 2,449,163, issued to T. A. Ford, and an article by K. E. Moller in *Brennstoff-Chemie,* 1, 10 (1966) both describe preparation of the acid, 3-chloro-2,2-dimethylpropionic acid, from 3-chloro-2-methylpropene and carbon monoxide by a Koch type of reaction catalyzed by boron trifluoride dihydrate. Both references are incorporated herein by reference.

4,4-Dimethyl-3-isoxazolidinone is a useful intermediate in the preparation of compouds of formula I generally, both those disclosed in U.S. Pat. No. 4,405,357 above, whether produced by Method A or Method B, and others which may have been disclosed elsewhere or are not yet known. Because of the commercial potential as herbicides of various species of formula I, there has been substantial interest in the development of alternative methods for preparing the precursor compound 4,4-dimethyl-3-isoxazolidinone.

The present invention provides a novel process for preparing 4,4-dimethyl-3-isoxazolidinone which comprises the following steps:

Step (a): intimately mixing 3-chloro-2-methylpropene or 1-chloro-2-methylpropene with carbon monoxide and boron trifluoride monohydrate at a pressure of at least 6.9 MPa (1000 psi), at least 2 molar portions of boron trifluoride monohydrate being used for each molar portion of 3-chloro-2-methylpropene or 1-chloro-2-methylpropene used, to give 3-chloro-2,2-dimethylpropionic acid, Step (b): converting the 3-chloro-2,2-dimethylpropionic acid to a lower alkyl 3-chloro-2,2-dimethylpropionate, Step (c): combining the lower alkyl 3-chloro-2,2-dimethylpropionate, an alkali metal hydroxide, and hydroxylamine at a temperature in the range of −20° to 5° C. in an alkanol solvent of 1 to 3 carbon atoms, at least one molar portion of hydroxylamine and 2 molar portions of alkali metal hydroxide being used for each molar portion of lower alkyl 3-chloro-2,2-dimethylpropionate employed, to give an alkali metal salt of 4,4-dimethyl-3-isoxazolidinone, and Step (d): converting the alkali metal salt of 4,4-dimethyl-3-isoxazolidinone to 4,4-dimethyl-3-isoxazolidinone.

The present process is illustrated by the following chemical equations:

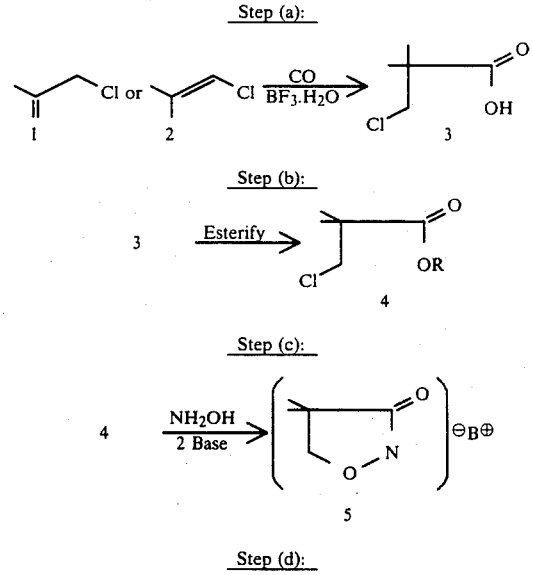

-continued

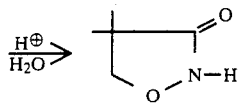

II

Step (a)

In step (a), 3-chloro-2-methylpropene (1) or 1-chloro-2-methylpropene (2) is reacted with carbon monoxide at elevated pressure in the presence of a catalyst boron trifluoride monohydrate to give 3-chloro-2,2-dimethylpropionic acid (3). The reaction is analogous to the Koch reaction described above and differs therefrom primarily in the use of substrate 2 and the catalyst boron trifluoride monohydrate.

Boron trifluoride monohydrate is known in the art, along with numerous other acidic materials, as being capable of catalyzing Koch-type reactions. (See, for example, the Moller article and U.S. Pat. No. 2,449,163 discussed above and U.S. Pat. No. 2,876,241, incorporated herein by reference.) However, boron trifluoride dihydrate has generally been the catalyst of choice in such reactions and has received much more attention in the literature than the monohydrate. It is therefore surprising that use of boron trifluoride monohydrate in the present process leads to superior yields, particularly where the substrate is 1-chloro-2-methylpropene. Generally, from 2 to 4 molar portions of the catalyst will be used for each molar portion of olefin substrate used.

The step (a) reaction may be conducted in the absence of a solvent or, if desired, in the presence of an inert solvent. Solvents known in the art to be useful for analogous reactions are suitable for use in the present process. For example, aliphatic hydrocarbons such as heptane, aromatic hydrocarbons such as xylene, and chlorinated hydrocarbons such as methylene chloride would be appropriate.

The Koch-type reaction of step (a) will generally be conducted at a pressure in the range of 6.9 to 27.6 MPa (1000 to 4000 psi), preferably from 10.4 to 17.3 MPa (1500 to 2500 psi). The reaction may be conducted in the cold, at room temperature, or at an elevated temperature, usually between 0° and 60° C., preferably from 25° to 50°. Advantageously, the reactants and catalyst will be intimately mixed together, for example by high-speed stirring preferably in the range of about 1600 to 2200 RPM, to minimize dimerization or polymerization of the chloro olefin.

Step (b)

In this step, 3-chloro-2,2-dimethylpropionic acid (3) is converted to a lower alkyl ester (4). The alkyl moiety is preferably of 1 to 3 carbon atoms and is advantageously a methyl group.

The conversion of 3-chloro-2,2-dimethylpropionic acid to the corresponding lower alkyl ester may be accomplished in one or more steps by routine methods known in the art. For example, the free acid 3 may be combined directly with a lower alkanol in the presence of a dehydrating agent such as dicyclohexylcarbodiimide to give the ester 4. Or the acid 3 may first be converted to a more reactive species such as the acid halide, which may then be treated with a lower alkanol to give the ester. Other esterification methods known in the art may also be used. An additional method for the preparation of methyl 3-chloro-2,2-dimethylpropionate is the general method for methyl esters of Clinton and Laskowski, *J. Am. Chem. Soc.*, 70, 3135 (1948), incorporated herein by reference. In this method, the free acid is treated with an excess of methanol and ethylene dichloride in the presence of concentrated sulfuric acid. A similar method, using methylene chloride, is exemplified below in Example V.

Step (c)

The lower alkyl ester of formula 4 above is combined with hydroxylamine and an alkali metal hydroxide base, preferably sodium hydroxide, to produce the alkali metal salt of 4,4-dimethyl-3-isoxazolidinone 5.

The reaction is conducted in an alkanol solvent of 1 to 3 carbon atoms, preferably methanol, and preferably in the absence of water. Methanol is most preferred because of its superior solubilizing capabilities with respect to the alkali metal hydroxide base. The presence of large quantities of water, which would hinder dissolution of the 4,4-dimethyl-3-isoxazolidinone substrate, will generally lead to drastically reduced yields. Satisfactory yields will generally be obtained with up to about 5% by volume of water present.

Preferably from 1.1 to 5 molar portions of hydroxylamine and from 2 to 4 molar portions of alkali metal hydroxide base are used for each molar portion of lower alkyl ester 4 used. Very good yields have been obtained with 1.5 to 2.5 molar portions of hydroxylamine and 2 to 3 molar portions of base for each molar portion of ester used.

The reaction of step (c) is conducted in the cold, generally at a temperature in the range of −20° to 5°, preferably −20° to −5° C.

In a preferred embodiment, step (c) is conducted by adding the lower alkyl 3-chloro-2,2-dimethylpropionate and a solution of the alkali metal hydroxide in an alkanol solvent of 1 to 3 carbon atoms simultaneously to a solution of the hydroxylamine in an alkanol solvent of 1 to 3 carbon atoms.

The alkanol solvent for hydroxylamine is preferably the same as the alkanol solvent for the alkali metal hydroxide base, but may be different. The alkanolic solution of hydroxylamine is conveniently prepared by treatment of a solution of a hydroxylamine salt, preferably the hydrochloride, in the alkanol solvent with a base. Preferred bases include sodium hydroxide, potassium hydroxide, ammonium hydroxide, ammonia, sodium bicarbonate, sodium carbonate, and potassium carbonate, especially sodium hydroxide.

Step (d)

The alkali metal salt of 4,4-dimethyl-3-isoxazolidinone produced in step (c) may be converted to 4,4-dimethyl-3-isoxazolidinone, compound II, by conventional means, for example by acidification of an aqueous solution of the alkali metal salt. Generally a mineral acid such as sulfuric, hydrochloric, or phosphoric acid will be used. However, organic acids, such as acetic acid, may also be used.

The four-step method described above, the individual steps (a) and (c), and all combinations of successive steps represent individual processes of the present invention.

A further aspect of the present invention relates to a method for producing 1-chloro-2-methylpropene, 2, a starting material in step (a) above, by isomerization of 3-chloro-2-methylpropene, 1, as illustrated in the following chemical equation.

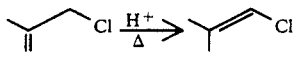

1 2

The isomerization of 1 to produce 2 is acid catalyzed. The use of aqueous 75% to 85% sulfuric or phosphoric acid as the catalyst has been found to give satisfactory results. A preferred catalyst is 80% sulfuric acid. Generally, from 0.02 to 1.0 g, preferably from 0.02 to 0.2 g., of the aqueous acid is used for each one gram of 3-chloro-2-methylpropene used. The reaction is advantageously conducted at a temperature in the range of about 35° to 75° C., preferably 40° to 60° C.

The conversion of 4,4-dimethyl-3-isoxazolidinone to a compound of formula I above may be accomplished by conventional methods, for example by alkylation with $RCH_2X$ wherein X is a good leaving group, as exemplified in Examples 30–33 of U.S. Pat. No. 4,405,357 discussed above.

The present invention is illustrated in greater detail in the following examples.

EXAMPLE I

Boron Trifluoride Monohydrate

Gaseous boron trifluoride (12.563 kg, 185.3 mol) was metered, via a dip tube extending below the surface, into 3.400 kg (188.8 mol) of stirred water. The reaction mixture temperature was kept between 4° and 35° C. by external cooling throughout the addition which required 12 hours and 41 minutes. A quantitative yield, 15.963 kg, of boron trifluoride monohydrate was obtained.

EXAMPLE II

1-Chloro-2-methylpropene from 3-Chloro-2-methylpropene

One thousand g (10.5 mol) of 95% pure 3-chloro-2-methylpropene was warmed to 40° C. with stirring. To this was added dropwise 50 g of aqueous 80% sulfuric acid over 3 hours (wt. ratio of sulfuric acid to 1-chloro-2-methylpropene is 0.05:1). The temperature of the reaction mixture was maintained at 49°–53° C. with external heating during the addition. The two phases were separated and the organic phase was stirred for 1 hour in the presence of 1.5 g of sodium carbonate and 10 mL of water. The aqueous carbonate phase was separated to leave 884 g of crude product as the organic phase. The crude product was found to contain 89.7% of 1-chloro-2-methylpropene by gas chromatographic analysis. Distillation using a five tray Oldershaw distilling system afforded 850.0 g of 1-chloro-2-methylpropene, bp. 68°–70° C., 91.5% purity by gas chromatographic analysis.

EXAMPLE III

3-Chloro-2,2-dimethylpropionic Acid from 3-Chloro-2-methylpropene

A 300 mL Hastalloy stainless steel high pressure reactor was charged with 112.0 g (1.30 mol) of boron trifluoride monohydrate. The reaction system was purged twice with carbon monoxide at 250 psi (1.746 MPa). The contents of the reactor were stirred at 2000 RPM and warmed to 40° C. Carbon monoxide was introduced into the system at a pressure of 2000–2300 psi (13.8 to 15.9 MPa). The system was allowed a 15 minute equilibration period, then 39.0 g (410 mmol) of 95% pure 3-chloro-2-methylpropene was added over 1 hour, 40 minutes. Upon complete addition, the reaction mixture was stirred for 30 minutes. The reaction mixture was poured onto 113 g of crushed ice, and the reaction vessel was washed with two portions of 100 mL each of methylene chloride. The methylene chloride washes were combined and added to the ice mixture. The reaction vessel was washed again with two portions of 100 mL each of methylene chloride, and these washes were set aside. The ice mixture was separated into organic and aqueous phases, and the aqueous phase was extracted with the two methylene chloride washes previously set aside. The organic phase from above and the methylene chloride extracts were combined, and the solvent removed by distillation using a one-inch, five tray Oldershaw distilling system to give 115 g of residue. Gas chromatographic analysis using p-xylene as an internal standard showed the residue to contain 37.65% by weight (43.3 g) of 3-chloro-2,2-dimethylpropionic acid, 77.6% yield.

EXAMPLE IV

3-Chloro-2,2-dimethylpropionic Acid from 1-Chloro-2-Methylpropene

A 2.0 L baffled autoclave was charged by vacuum with 1.045 kg (12.2 mol) of boron trifluoride monohydrate. The reaction system was purged twice with carbon monoxide at 50 to 100 psi (344.7 to 689.5 kPa). The contents of the reactor were stirred at 1800 to 2000 RPM and warmed to 40° to 50° C. Carbon monoxide was introduced into the system at a pressure of 2000 psi (13.8 MPa). After a short equilibration period, 362.0 g (4.0 mol) of 1-chloro-2-methylpropene was added by way of a tube extended below the surface of the reaction mixture. The addition was made over 4.0 hours, after which the reaction mixture was stirred for an additional 15 minutes. The autoclave was vented and the contents poured onto 540 g of ice. The autoclave was washed with two portions of 500 mL each of methylene chloride. The methylene chloride washes were added to the ice mixture. When the ice melted, the aqueous phase was separated and washed with 500 mL of methylene chloride. The methylene chloride wash was combined with the organic phase, and the whole was concentrated to give 844.0 g of residue. Gas chromatographic analysis using p-xylene as an internal standard showed the residue to contain 48.60% by weight (410.2 g) of 3-chloro-2,2-dimethylpropionic acid, a 75% yield. The residue was distilled using a one-inch, ten tray Oldershaw distilling system to give 402.0 g (74.2% yield) of 3-chloro-2,2-dimethylpropionic acid, bp. 116°–120° C., 98% purity by gas chromatographic analysis.

EXAMPLE V

Methyl 3-Chloro-2,2-dimethylpropionate

This compound was prepared by a method similar to the general method for methyl esters of Clinton and Laskowski, *J. Am. Chem. Soc.*, 70, 3135 (1948).

A stirred solution of 137.0 g (1.0 mol) of 3-chloro-2,2-dimethylpropionic acid, 96.0 g (3.0 mol) of methanol, and 27.6 g (0.28 mol) of concentrated sulfuric acid in 300 mL of methylene chloride was heated at reflux temperature for 16 hours. The reaction mixture was allowed to cool to room temperature and stand for 60 hours. The mixture was stirred with 300 g of ice/water and the two layers separated. The organic layer was dried over magnesium sulfate, filtered, and the filtrate concentrated under reduced pressure to give 151 g of a residual oil. The oil was distilled under reduced pressure to give 102.5 g of 99% pure methyl 3-chloro-2,2-dimethylpropionate, bp. 73°-74° C./37 mm (4.93 kPa).

EXAMPLE VI

4,4-Dimethyl-3-isoxazolidinone

Hydroxylamine hydrochloride, 280.0 g (4.0 mol), was dissolved in 1000 mL of methanol. The stirred solution was kept below 30° C. while four portions of 40.0 g each (4.0 mol) of sodium hydroxide were added over 1 hour. Upon complete addition, the solution was stirred at room temperature for 16 hours.

In a separate reaction vessel, under a nitrogen atmosphere, four portions of 40.0 g each (4.0 mol) of sodium hydroxide were added to 850 mL of stirred methanol. Upon complete addition, the solution was stirred at room temperature for 16 hours.

To the hydroxylamine-methanol solution, cooled to −10° C., were added simultaneously and dropwise 306.0 g (2.0 mol) of methyl 3-chloro -2,2-dimethylpropionate and the 850 mL of methanolic sodium hydroxide solution above. The complete addition was made over 12 hours, and the temperature of the reaction mixture during the addition was maintained between −10° and −7° C. Upon complete addition, the reaction mixture was stirred for an additional 12 hours at −7° C., then 200 mL of water was added dropwise over 25 minutes. The temperature of the reaction mixture was adjusted to −5° C., and 175.0 g (2.4 mol) of methyl ethyl ketone was added dropwise over 1 hour, to remove any excess hydroxylamine. Methanol, approximately 1.60 L, was removed from the reaction mixture at 40° C./100 mm (13.3 kPa). An equal amount of water was added to the reaction mixture and the resulting solution was extracted with four portions of 500 mL each of methylene chloride to remove any hydroxylamine-methyl ethyl ketone reaction product. The aqueous layer weighed 2.154 kg.

A 215 g aliquot of the aqueous layer (10% of the total) was removed and the pH adjusted to 2 with concentrated hydrochloric acid. The mixture was extracted with four 50 mL portions of methylene chloride, and the combined extracts were concentrated under reduced pressure at 50° C. to give 22.2 g of crude 4,4-dimethyl-3-isoxazolidinone, 81.6% purity by gas chromatography. Based on this analysis, the amount of 4,4-dimethyl-3-isoxazolidinone in the aliquot was 18.115 g, and the estimated overall yield is 181.2 g or 78.7%.

A second 215 g aliquot of the aqueous layer above was treated in a similar manner to give 22.7 g of crude 4,4-dimethyl-3-isoxazolidinone, 83.5% purity by gas chromatography. Based on this analysis, the amount of 4,4-dimethyl-3-isoxazolidinone in the aliquot was 18.954 g, and the estimated overall yield is 189.5 g or 82.3%.

A third 215 g aliquot of the aqueous layer was taken, and the pH adjusted to 5 with phosphoric acid. The mixture was extracted with methylene chloride and concentrated as described above to give 22.2 g of crude 4,4-dimethyl-3-isoxazolidinone, 83.6% purity by gas chromatography. Based on this analysis, the amount of 4,4-dimethyl-3-isoxazolidinone in the aliquot was 18.559 g, and the estimated overall yeild is 185.6 g or 80.6%.

A fourth 215 g aliquot of the aqueous layer was removed and the pH adjusted to 4.8 with phosphoric acid in the manner described above to give 22.3 g of crude 4,4-dimethyl-3-isoxazolidinone, 82.5% purity by gas chromatography. Based on this analysis, the amount of 4,4-dimethyl-3-isoxazolidinone in the aliquot was 18.398 g, and the estimated overall yield is 184.0 g or 79.9%.

We claim:

1. A process for preparing 3-chloro-2,2-dimethylpropionic acid which comprises intimately mixing 1-chloro-2-methylpropene, carbon monoxide, and boron trifluoride monohydrate at a pressure of at least 6.9 MPa, at least 2 molar portions of boron trifluoride monohydrate being used for each molar portion of 1-chloro-2-methylpropene used, to give 3-chloro-2,2-dimethylpropionic acid.

2. The process of claim 1 wherein the pressure is in the range of 6.9 to 27.6 MPa, the temperature is in the range of 0° to 60° C., and from 2 to 4 molar portions of boron trifluoride monohydrate are used for each molar portion of 1-chloro-2-methylpropene used.

3. The process of claim 2 wherein the pressure is in the range of 10.4 to 17.3 MPa and the temperature is in the range of 25° to 50° C.

4. The process of claim 1 which contains as a first step the additional step of treating 3-chloro-2-methylpropene with about 75 to 85% aqueous sulfuric or phosphoric acid at a temperature in the range of about 35° to 75° C., from 0.02 to 1.0 portion by weight of 75 to 85% aqueous acid being used for each portion by weight of 3-chloro-2-methylpropene used, to produce 1-chloro-2-methylpropene.

5. The process of claim 4 wherein from about 0.02 to 0.2 portion by weight of aqueous acid is used for each portion by weight of 3-chloro-2-methylpropene used.

6. A process for preparing 4,4-dimethyl-3-isoxazolidinone which comprises the steps of (a) intimately mixing 1-chloro-2-methylpropene with carbon monoxide and boron trifluoride monohydrate at a pressure of at least 6.9 MPa, at least 2 molar portions of boron trifluoride monohydrate being used for each molar portion of 3-chloro-2-methylpropene or 1-chloro-2-methylpropene used, to give 3-chloro-2,2-dimethylpropionic acid, (b) converting the 3-chloro-2,2-dimethylpropionic acid to methyl 3-chloro-2,2-dimethylpropionate, (c) adding the methyl 3-chloro-2,2-dimethylpropionate and a solution of sodium hydroxide in methanol simultaneously to a solution of hydroxylamine in methanol at a temperature in the range of −20° to 5° C. , from 1.1 to 5.0 molar portions of hydroxylamine and from 2 to 4 molar portions of sodium hydroxide being used for each molar portion of methyl 3-chloro-2,2-dimethylpropionate used, to give the sodium salt of 4,4-dimethyl-3-isoxazolidinone, and (d) converting the sodium salt of 4,4-dimethyl-3-isoxazolidinone to 4,4-dimethyl-3-isoxazolidinone.

7. The process of claim 6 wherein step (a) is conducted at a pressure in the range of 6.9 to 27.6 MPa and a temperature in the range of 0° to 60° C., and from 2 to 4 molar portions of boron trifluoride monohydrate are used for each molar portion of 1-chloro-2-methylpropene used.

8. The process of claim 7 wherein in step (a) the pressure is in the range of 10.4 to 17.3 MPa and the temperature is in the range of 25° to 50° C.

9. The process of claim 6 wherein in step (c) from 1.5 to 2.5 molar portions of hydroxylamine and from 2 to 3 molar portions of sodium hydroxide are used for each molar portion of methyl 3-chloro-2,2-dimethylpropionate used, and the temperature is in the range of −20° to −5°, and the solution of hydroxylamine in methanol is prepared by treatment of a solution of hydroxylamine hydrochloride in methanol with a base.

10. The process of claim 9 wherein the solution of hydroxylamine hydrochloride is treated with sodium hydroxide.

11. A process for preparing 4,4-dimethyl-3-isoxazolidinone which comprises (a) treating a solution of hydroxylamine hydrochloride in methanol with sodium hydroxide to produce a solution of hydroxylamine in methanol, (b) adding methyl 3-chloro-2,2-dimethylpropionate and a solution of sodium hydroxide in methanol simultaneously to the solution of hydroxylamine in methanol at a temperature in the range of −20° to −5° C., from 1.5 to 2.5 molar portions of hydroxylamine and from 2 to 3 molar portions of sodium hydroxide being used for each molar portion of methyl 3-chloro-2,2-dimethylpropionate used, to give the sodium salt of 4,4-dimethyl-3-isoxazolidinone, and (c) treating the sodium salt of 4,4-dimethyl-3-isoxazolidinone with a mineral acid or acetic acid in the presence of water to give 4,4-dimethyl-3-isoxazolidinone.

12. The process of claim 11 in which in step (c) the sodium salt is treated with hydrochloric acid.

* * * * *